United States Patent [19]

Shapland et al.

[11] Patent Number: 5,286,254
[45] Date of Patent: Feb. 15, 1994

[54] DRUG DELIVERY APPARATUS AND METHOD

[75] Inventors: James E. Shapland; Mark B. Knudson, both of Shoreview; Jin Shimada, Falcon Heights, all of Minn.

[73] Assignee: CorTrak Medical, Inc., Roseville, Minn.

[21] Appl. No.: 937,464

[22] Filed: Aug. 28, 1992

Related U.S. Application Data

[63] Continuation-in-part of Ser. No. 705,731, May 24, 1991, which is a continuation-in-part of Ser. No. 637,299, Jan. 3, 1991, abandoned, which is a continuation-in-part of Ser. No. 538,961, Jun. 15, 1990, abandoned.

[51] Int. Cl.$^5$ ............................................. A61B 17/36
[52] U.S. Cl. ..................................... 604/21; 604/20; 604/96
[58] Field of Search ................................. 604/20–22, 604/52–53, 96–103; 128/24 AA

[56] References Cited

U.S. PATENT DOCUMENTS

| | | |
|---|---|---|
| 578,611 | 3/1897 | Rively . |
| 725,731 | 4/1903 | Linn . |
| 873,021 | 12/1907 | Cool . |
| 2,123,980 | 7/1938 | Warwick . |
| 2,499,045 | 8/1948 | Walker et al. . |
| 3,542,014 | 11/1970 | Peronneau . |
| 3,865,108 | 2/1975 | Hartop . |
| 4,126,134 | 11/1978 | Bolduc et al. . |
| 4,137,906 | 2/1979 | Akiyama et al. . |
| 4,202,346 | 5/1980 | Granier . |
| 4,323,071 | 4/1982 | Simpson et al. . |
| 4,338,942 | 7/1982 | Fogarty . |
| 4,364,392 | 12/1982 | Strother et al. . |
| 4,383,529 | 5/1983 | Webster . |
| 4,403,612 | 9/1983 | Fogarty . |
| 4,411,648 | 10/1983 | Davis et al. . |
| 4,416,274 | 11/1983 | Jacobsen et al. . |
| 4,417,576 | 11/1983 | Baran . |
| 4,456,012 | 6/1984 | Lattin . |
| 4,509,523 | 4/1985 | Pevsner . |
| 4,551,132 | 11/1985 | Pasztor et al. . |
| 4,573,966 | 3/1986 | Weikl et al. . |

(List continued on next page.)

FOREIGN PATENT DOCUMENTS

| | | |
|---|---|---|
| 299698 | 1/1989 | European Pat. Off. . |
| 372088 | 6/1990 | European Pat. Off. . |
| 147314 | 4/1981 | Fed. Rep. of Germany . |
| 3915636 | 4/1990 | Fed. Rep. of Germany . |
| 2582946 | 12/1986 | France . |
| 49-132888 | 12/1974 | Japan . |
| WO89/01794 | 3/1989 | PCT Int'l Appl. . |
| WO91/16945 | 11/1991 | PCT Int'l Appl. . |
| WO91/19529 | 12/1991 | PCT Int'l Appl. . |

(List continued on next page.)

OTHER PUBLICATIONS

Antich, *Journal of Orthopaedic and Sports Physical Therapy,* 4(2), 99–102 (1982).

(List continued on next page.)

*Primary Examiner*—C. Fred Rosenbaum
*Assistant Examiner*—Michael Rafa
*Attorney, Agent, or Firm*—Merchant, Gould, Smith, Edell, Welter & Schmidt

[57] ABSTRACT

A drug delivery apparatus and method for delivering a drug locally to internal body tissue. The invention contemplates positioning a drug delivery device in a body passageway or within body tissue and then selectively introducing a selected drug so that it is transported across a drug transport wall of the device for direct contact with the passageway wall or body tissue. A further aspect of the present invention involves treating a dilated vessel in the area of a stenotic lesion with a fixative or other drug to render the vessel biologically inert and to form a biological stent or prevent restenosis using specifically selected drugs. A still further aspect of the present invention involves treating a tumor or local or regional tissue mass with antitumor sensitizing agents, biological modifiers, antibiotics or other types of drugs by delivery of the drug to the tumor or tissue area directly or through the passageway wall.

17 Claims, 6 Drawing Sheets

U.S. PATENT DOCUMENTS

| | | |
|---|---|---|
| 4,582,181 | 4/1986 | Samson . |
| 4,606,337 | 8/1986 | Zimmermann et al. . |
| 4,608,984 | 9/1986 | Fogarty . |
| 4,610,662 | 9/1986 | Weikl et al. . |
| 4,636,195 | 1/1987 | Wolinsky . |
| 4,663,358 | 5/1987 | Hyon et al. ............................ 521/64 |
| 4,689,041 | 8/1987 | Corday et al. . |
| 4,693,704 | 9/1987 | Ogita . |
| 4,698,058 | 10/1987 | Greenfeld et al. . |
| 4,705,507 | 11/1987 | Boyles . |
| 4,714,460 | 12/1987 | Calderon . |
| 4,733,665 | 3/1988 | Palmaz . |
| 4,744,366 | 5/1988 | Jang . |
| 4,767,402 | 8/1988 | Kost et al. . |
| 4,776,337 | 10/1988 | Palmaz . |
| 4,787,888 | 11/1988 | Fox . |
| 4,800,882 | 1/1989 | Gianturco . |
| 4,819,637 | 4/1989 | Dormandy, Jr. et al. . |
| 4,819,751 | 4/1989 | Shimada et al. . |
| 4,824,436 | 4/1989 | Wolinsky . |
| 4,832,688 | 5/1989 | Sagae et al. . |
| 4,866,050 | 9/1989 | Ben-Amoz . |
| 4,948,587 | 8/1990 | Kost et al. . |
| 4,994,033 | 2/1991 | Shockey et al. . |
| 5,000,734 | 3/1991 | Boussignac et al. . |
| 5,007,897 | 4/1991 | Kalb et al. . |
| 5,041,107 | 8/1991 | Heil, Jr. . |
| 5,047,028 | 9/1991 | Qian ....................................... 606/49 |
| 5,087,243 | 2/1992 | Avital . |
| 5,087,244 | 2/1992 | Wolinsky et al. . |
| 5,102,402 | 4/1992 | Dror et al. . |
| 5,236,413 | 8/1993 | Feiring ................................... 604/21 |

FOREIGN PATENT DOCUMENTS

| | | |
|---|---|---|
| 588870 | 6/1977 | Switzerland . |
| 645273 | 9/1984 | Switzerland . |
| 1003853 | 3/1983 | U.S.S.R. ................................ 604/20 |
| 1069826 | 1/1984 | U.S.S.R. . |
| 1069827 | 1/1984 | U.S.S.R. . |
| 1146057 | 3/1985 | U.S.S.R. ................................ 604/20 |
| 1410973 | 7/1988 | U.S.S.R. . |

OTHER PUBLICATIONS

Brand, *Cardio,* November, 48–56 (1989).
Ellman et al., *Investigative Radiology,* 19(5), 416–423 (1984).
Goldman et al., *Atherosclerosis,* 65, 215–225 (1987).
Jorgensen et al., *The Lancet,* May 20, 1106–1108 (1989).
Klimberg et al., *Urology,* 33(2), 153–158 (1989).
Layer et al., *Br. J. Surg.,* 71, 709–710 (1984).
Okada et al., *Stroke,* 19(12), 1470–1476 (1988).
Okada et al., *Neurosurgery,* 25(6), 892–898 (1989).
Sheehan and Hrapchak, *Theory and Practice of Histotechnology,* Ch. 2, 40–50 1984).
Skauen et al., *International Journal of Pharmaceutics,* 20, 235–245 (1984).
Wolinsky et al., *JAAC,* 15(2), 475–481 (1990).
*BBI Newsletter,* 13(5), 85–91 (1990).

DRUG DELIVERY APPARATUS AND METHOD

REFERENCE TO CO-PENDING APPLICATION

This application is a continuation-in-part of U.S. application Ser. No. 07/705,731, filed May 24, 1991, which is a continuation-in-part of U.S. application Ser. No. 637,299, filed Jan. 3, 1991 abandoned, which in turn is a continuation-in-part of U.S. application Ser. No. 538,961, filed Jun. 15, 1990 abandoned.

BACKGROUND OF THE INVENTION

1. Field of the Invention

The present invention relates generally to a drug delivery apparatus and method, and more particularly, to an apparatus and method for selectively and locally delivering a drug to internal body tissue. More specific applications of the present invention relate to an apparatus and method for limiting restenosis of natural or an artificially dilated blood vessel and localized treatment of tumors or other tissue.

2. Description of the Prior Art

Many techniques currently exist for delivering drugs or other medicaments to body tissue. These include, among possible others, oral administration, injection directly into body tissue such as through an intramuscular injection or the like, topical or transcutaneous administration where the drug is passively absorbed, or caused to pass, into or across the skin or other surface tissue and intravenous administration which involves introducing a selected drug directly into the blood stream.

Except for topical or transcutaneous administration, the above drug delivery systems tend to be systemic. In other words, administration of the drug is delivered throughout the body by the blood stream. Although transcutaneous drug delivery systems tend to be localized delivery systems in that the drug is delivered locally to a selected area, such drug delivery systems are also, by definition, limited to application of a drug externally through the patient's skin or other surface tissue. Thus, the above described drug delivery systems are generally not appropriate for the localized treatment of internal body tissue.

Although many medical situations are satisfactorily treated by the general systemic administration of a drug, there are a great many treatments which could be facilitated and/or improved by the ability to deliver or administer a drug locally to a selected portion of internal body tissue, without appreciably affecting the surrounding tissue.

One example is the ability to treat the dilated vessel in percutaneous transluminal coronary angioplasty (PTCA), and thus limit or prevent restenosis. In PTCA, catheters are inserted into the cardiovascular system under local anesthesia and an expandable balloon portion is then inflated to compress the atherosclerosis and dilate the lumen of the artery. Despite the general success of such PTCA procedures, high restenosis rates (reported to be as high as 47%) continue to be a major problem. Various techniques have been tried to treat stenosed vessels including the use of lasers, application of heat and the use of intravascular stents. However, many of these are still under investigation with mixed results, while others have generally not been successful. The ability to administer a drug locally to the dilated portion of the artery in PTCA procedures, without significantly affecting other tissues, would greatly enhance the ability to address the restenosis problem.

A second example of specific application for a local drug delivery system for delivering a drug to an internal body tissue is in the treatment of cancerous tumors or the like. In the treatment of such tumors, an objective is to administer the cancer drug so that it localizes, as much as possible, in the tumor itself. Such drugs are commonly administered systemically through the blood stream. Various means are then utilized for causing the drug to localize in the cancer tumor. Nevertheless, significant portions of the drug still circulate through the blood stream, thereby affecting noncancerous tissue, producing undesirable side effects, and limiting the dosages of the drug which can be safely administered.

Accordingly, there is a need in the art for a method and apparatus for delivering a drug selectively and locally to internal body tissue, without significantly affecting other tissue. There is a further need for such a system and method for the localized treatment of internal body tissues to limit restenosis following PTCA, to treat cancerous tumors or the like, or to treat various other medical situations.

SUMMARY OF THE INVENTION

In accordance with the present invention, an apparatus and method is provided for delivering a drug or combination of drugs selectively and locally to an internal body tissue. More specifically, the invention involves an apparatus and method for delivering a drug or combination of drugs substantially transversely to the longitudinal axis of a body passageway such as blood vessel, urinary tract, intestinal tract, kidney ducts, etc., in order to treat a localized region of the passageway itself or to treat a localized region or tissue located adjacent to the passageway. The invention also involves an apparatus and method for delivering a drug or combination of drugs directly to an internal body tissue.

In the preferred embodiment, the apparatus includes a flexible member adapted for insertion into the body passageway or tissue and a drug delivery means connected with the flexible member for delivering the drug to or through a local area of the passageway wall or tissue. The drug delivery means includes a drug transport wall for engagement with a local area of the passageway wall or tissue and a drug chamber for receiving a selected drug. The chamber is defined in part by the drug transport wall which is constructed of a material that permits selective transport of a drug therethrough, i.e. constructed of at least perforated, permeable, microporous or semipermeable material through which the drug is intended to selectively pass, that is, selectively permeable.

Preferably, in one embodiment the drug delivery means includes a modified catheter balloon or bag. The modified catheter balloon contacts the inner surface of the passageway wall and defines the localized passageway area to or through which the drug is to be administered.

In a second embodiment, to deliver a drug to an internal body tissue, the preferred apparatus includes a catheter body connected with a drug delivery component having a drug delivery passageway, an outer wall and a selectively permeable outer membrane portion.

The method of the present invention involves positioning a drug delivery member such as a modified catheter balloon in a body passageway such that the delivery member or balloon traverses the desired localized area of administration. The balloon is then inflated or otherwise expanded to define a local drug administration zone in the passageway. This involves introducing a selected drug into or through the localized zone or passageway. The method for delivering a drug to an internal body tissue involves positioning the drug delivery component at a target area of an internal body tissue and transporting the selected drug across the selectively permeable outer membrane of the drug delivery component and into the internal body tissue target area.

A specific application of the apparatus and method of the present invention involves the treatment of a dilated vessel to prevent restenosis following PTCA. In the preferred embodiment and procedure, this involves administering a fixation solution or fixative to the passageway walls in the localized area. Administration of the fixative in this area renders the dilated artery biologically inert, resulting in a certain degree of hardening and the production of a biological stent. A further specific application of the apparatus and method of the present invention is in the treatment of cancerous tumors or other internal body tissue adjacent to a body passageway, such as the prostrate.

Accordingly, it is an object of the present invention to provide a drug delivery apparatus and method for delivering a drug or combination of drugs locally to internal body tissue.

Another object of the present invention is to provide an apparatus and method for delivering a drug or combination of drugs locally to internal body tissue through selected portions of a body passageway wall.

Another object of the present invention is to provide an apparatus and method for treatment of dilated vessels to prevent or limit restenosis following PTCA procedures.

Another object of the present invention is to provide an apparatus and method for local treatment of cancerous tumors or other internal body tissues.

A still further object of the present invention is to provide a modified dilation catheter having localized drug delivery capabilities for limiting restenosis and for the delivery of drugs locally to internal body tissues.

These and other objects of the present invention will become apparent with reference to the drawings, the description of the preferred embodiment and method and the appended claims.

DESCRIPTION OF THE DRAWINGS

FIGS. 12a and 12b show a cross-section of selectively permeable microporous membrane of the catheter of FIG. 11 in cross-section along line 11—11. FIG. 12a shows an isotropic (asymmetric) structure. FIG. 12b shows a symmetric structure.

DESCRIPTION OF THE PREFERRED AND ALTERNATE EMBODIMENTS AND METHODS

FIGS. 1-8 illustrate the preferred and various alternate designs of the drug delivery apparatus in accordance with the present invention. In general, this apparatus provides a means and a system for delivering a drug or combination of drugs to or through a localized area of a passageway in order to treat the localized area of the passageway or to treat a localized area of tissue located adjacent to the passageway, with minimal, if any, undesirable effect on other body tissue. The drug delivery apparatus includes a modified catheter balloon design which can be used in conjunction with existing catheters. The term catheter as used in the present application is intended to broadly include any medical device designed for insertion into a body passageway to permit injection or withdrawal of fluids, to keep a passage open or for any other purpose. It is contemplated that the drug delivery apparatus of the present invention has applicability for use with any body passageways including, among others, blood vessels, urinary tract, intestinal tract, kidney ducts, wind pipe and the like.

Figure 9:
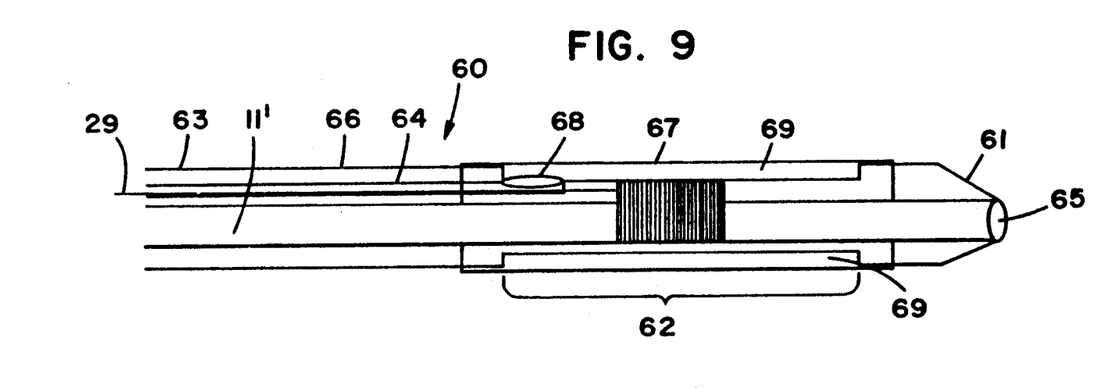
FIG. 9 is a fragmentary view, partially in section, of a still further alternate design of a drug delivery apparatus in accordance with the present invention in the form of a catheter with a drug delivery component to transport a drug to an internal body tissue.
Figure 10:
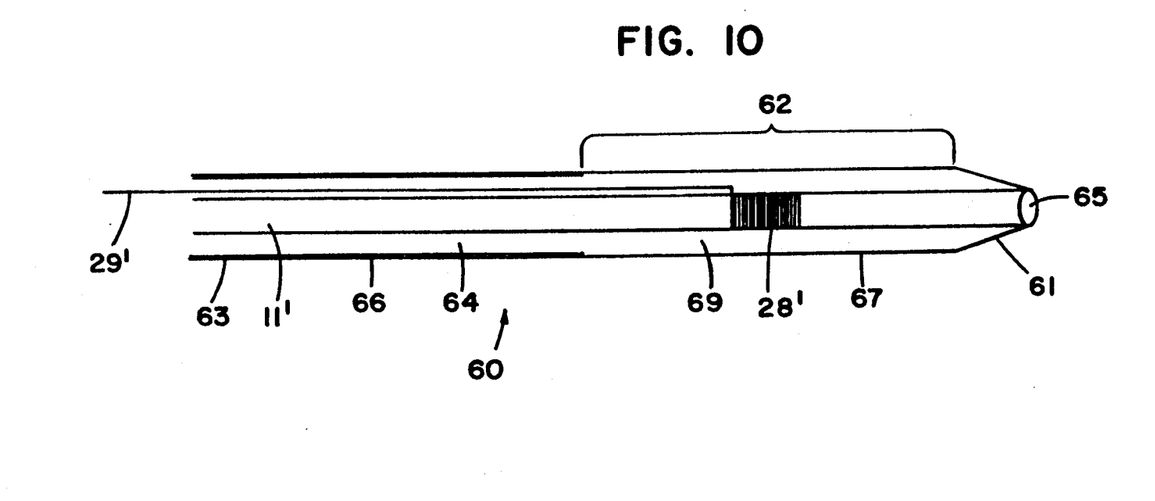
FIG. 10 is a fragmentary view, partially in section, of a still further alternate design of the drug delivery apparatus shown in FIG. 9 for drug transport to an internal body tissue in which a selectively permeable membrane forms a portion of the outer wall of the drug delivery component.

FIGS. 9 and 10 illustrate further alternate designs of the drug delivery apparatus in accordance with the present invention. The embodiments shown in these figures are specifically designed to provide means and a system for delivering a drug or combination of drugs to a localized area of an internal body tissue. For this purpose the apparatus includes a flexible catheter connected to a drug delivery component having a fluid delivery passageway with an outer wall and selectively permeable outer membrane portion through which a drug passes to an internal body tissue target area.

In particular, catheters are commonly used in percutaneous transluminal coronary angioplasty (PTCA) procedures to dilate stenosed blood vessels or arteries. These include so-called over the wire catheters of the type illustrated generally in U.S. Pat. No. 4,323,071, the disclosure of which is incorporated herein by reference, and so-called fixed wire catheters of the type illustrated in U.S. Pat. No. 4,582,181, the disclosure of which is incorporated herein by reference. These catheters may be modified according to the present invention.

In order to illustrate the method aspect of treating a localized area of a passageway, the specific application of the present invention to the reduction of restenosis will be described. Following a discussion of reducing restenosis, the present invention will be applied to the treatment of tumors.

As indicated in the discussion earlier, percutaneous transluminal coronary angioplasty (PTCA) has been demonstrated to be a highly successful procedure for the treatment of atherosclerosis and other diseases and conditions tending to narrow arterial passageways. In normal PTCA procedure, a dilatation catheter is advanced along an artery to the desired position in the arterial system. The catheter includes an inflatable balloon at its distal end and means for inflating the balloon. When the balloon is positioned so that it traverses or crosses a stenotic lesion, the balloon is inflated to compress the atherosclerosis and expand the artery in a direction generally perpendicular to its wall, thereby dilating the lumen of the artery. Following this procedure, the balloon is deflated and the catheter withdrawn.

Despite the generally excellent success of PTCA, relatively high restenosis (the tendency of the dilated artery to close) rates continue to be a major problem. Restenosis can include abrupt reclosure resulting from thrombotic occlusion, vasospasms, or the like as well as the more common occurrence of gradual restenosis.

In accordance with the method of the present invention, a drug referred to as a fixation solution or a fixative is delivered locally to the dilated portion of the vessel to render the vessel wall biologically inert to prevent or reduce reactions that lead to reclosure. Because of the nature of the fixative and its ability to inactivate living cells and render the tissue in which it comes into contact biologically inert, it is essential that such fixative be exposed only to that portion of the arterial wall which has been dilated. A preferred method and apparatus for delivering the fixative locally to the dilated vessel is via a modified catheter balloon. The balloon catheter that delivers the drug may be the same balloon catheter that dilates the vessel, thus combining both functions in one catheter. Alternatively, a vessel may be dilated first with a catheter designed specifically for dilation, followed by insertion of a second catheter for drug delivery. One embodiment of a modified balloon useful for either approach is illustrated in FIGS. 1 and 2.

Figure 1:
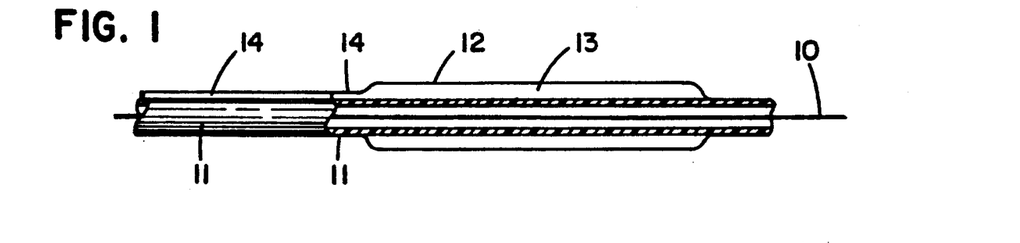
FIG. 1 is a fragmentary view, partially in section, of a first embodiment of the drug delivery apparatus of the present invention in the form of a catheter with a modified dilatation balloon in its deflated state.

FIG. 1 illustrates the distal end of a catheter with the modified catheter balloon in its deflated state. The catheter includes a guide wire 10, an elongated, flexible catheter body 11, a drug delivery means in the form of a balloon 12 positioned on the catheter body 11 near its distal end and a balloon lumen or passageway 14 extending along the catheter body 11 to the proximal end of the body 11 for inflation and deflation of the balloon 12. In the preferred embodiment, the material from which the balloon 12 is constructed is a permeable or semipermeable material which is effective to permit transport or passage of the fixative or other drug across the balloon surface as a result of an appropriate driving force.

The structure of the guide wire 10, the catheter body 11 and the balloon lumen 14 is similar to conventional catheter design which is known in the art and an example of which is shown in U.S. Pat. No. 4,323,071. The balloon 12 of FIG. 1, however, is distinguishable from conventional catheter balloons in that the balloon 12 is constructed from a material which selectively permits the transport or passage of a drug or fixative across the balloon surface.

Figure 2:
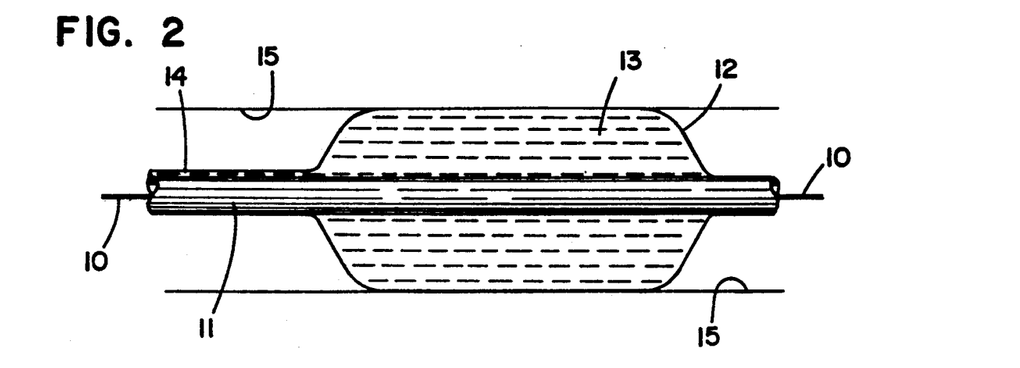
FIG. 2 is a fragmentary view, partially in section, of the drug delivery apparatus of FIG. 1 positioned in a blood vessel with the dilatation balloon in its inflated state.

FIG. 2 illustrates the drug delivery apparatus of FIG. 1 with the balloon 12 in its inflated state within an arterial vessel in which the vessel walls are indicated by the reference numeral 15. During PTCA procedures, the guide wire 10 is first inserted into the selected artery to a point past the stenotic lesion. The dilatation catheter including the catheter body 11 and balloon 12 is then advanced along the guide wire 10 to the desired position in the arterial system in which the balloon portion 12 traverses or crosses the stenotic lesion. The balloon 12 is then inflated by introducing an inflation fluid through the balloon lumen 14 into the interior chamber 13 of the balloon 12. During inflation, the outer surfaces of the balloon 12 press outwardly against the inner surfaces of the vessel wall 15 to expand or dilate the vessel in the area of the stenotic lesion. In accordance with the present invention, and in particular in accordance with the embodiment of FIGS. 1 and 2, the balloon 12 is inflated by introducing a fixation or other drug solution through the balloon lumen 14 and into the interior of the balloon portion 12. As a result of at least a portion of the balloon 12 being constructed of a permeable or semipermeable membrane, the pressure of the drug or fixative within the balloon 12 causes the drug or fixative to be transported across the walls of the balloon 12 into direct contact with the vessel wall 15.

Alternatively, the catheter of FIGS. 1 and 2 may be used after dilation has already been effected by another catheter earlier used to dilate the vessel. In this case, the fixative delivering catheter is expandable in order to bring the balloon 12 in contact with the vessel wall for drug delivery.

In the preferred embodiment, it is contemplated that the material from which the balloon of FIGS. 1 and 2 is constructed will be a semipermeable membrane material such as dialysis membrane (Cordis Dow 3500-cellulose acetate and Cordis Dow cellulose regenerated from acetate; anisotropic polyacrylonitrile available from Ashaki Medical). It is contemplated, however, that various other permeable, microporous or semipermeable materials may also be used including, without limitation, cellulose, cellulose acetate, polyvinyl chloride, polysulfone, polyacrylonitrile, silicon, polyurethanes, natural and synthetic elastomers. Examples of suitable microporous membranes are polyester, polyolefin, a fluorpolymer, or the like having pore sizes smaller than 1 micron and preferably from about 10 Å to 1 micron, with a nominal pore size of about 150 Å.

It is contemplated that the particular material from which the balloon 12 is constructed will depend to some extent on the specific composition of the fixative or other drug to be delivered as well as the transport or driving pressures which are developed within the balloon chamber 13. In the structure of FIGS. 1 and 2, the preferred material from which the balloon 12 is constructed is an elastomer and the pressure generated within the balloon chamber 13 to result in transport of the drug or fixation solution across the balloon walls is between about 1 and about 90 psi.

A fixative or fixation agent is a compound or composition known in the art as a fixative. A fixative functions, among other things, to kill, penetrate and harden fresh tissues, to set the tissues so that they will not be altered by subsequent biological or other processing and to render the cell constituents insoluble. Fixatives are commonly used for stabilizing and fixing tissue at the moment such tissue is exposed to the fixative so that histologic slides of the tissue can be prepared or the tissue can otherwise be preserved for examination.

The particular fixative or fixation solution as contemplated by the present invention must be able to rapidly penetrate the plaque and vascular tissue of the vessel in the area of the stenotic lesion. It should quickly kill or otherwise preserve the tissue, while hardening the vascular structure. Such fixation maintains the vessel in an "opened" or dilated condition and prevents or substantially reduces reclosure due to vasospasm or other abrupt reclosure mechanisms. Such fixation also retards or stops the biological processes which lead to gradual restenosis. The preferred fixative should also have rapid, specific action in high concentrations, while generally nontoxic actions in lower concentrations.

Current fixatives include:
Glutaraldehyde
Formaldehyde
Acetaldehyde
Ethyl Alcohol In accordance with the preferred apparatus and method of the present invention, the fixation solution may contain compounds or drugs to reduce vasomotor action (calcium antagonists) and inflammatory response (steroids) as well as antiplatelet inhibitors and anticoagulants. Calcium antagonists may include materials such as diltiazem HCl, nifedipine and verapamil HCl, steroids such as dexamethasone and specific nonsteroidal anti-inflammatory agents. Antiplatelet inhibitors and anticoagulants may include materials such as heparin, dipyridamole, papaverine HCl, ethaverine HCl and prostacyclin inhibitors. It is also contemplated that agents inhibiting smooth muscle and fibroblast proliferation which is a primary factor in restenosis, or agents tending to reduce collagen response to injury could also be used either with or without the fixation agent. Fibroblast proliferation inhibiting agents may also be included as well as collagen response reduction agents. It is still further contemplated that compounds which reduce platelet aggregation may also be beneficial to administer with a fixation solution. Also, antitumor or other antimitogenic drugs can be used for prevention of restenosis.

The formulation for the preferred fixative solution in accordance with the present invention is 2% by volume glutaraldehyde in normal saline solution. A second preferred fixative solution includes formalin at a concentration of about 10% in a normal saline solution.

Figure 3:
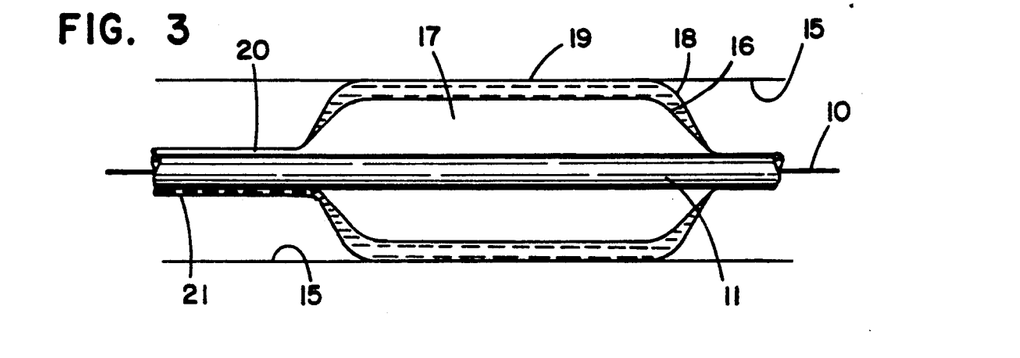
FIG. 3 is a fragmentary view, partially in section, of an alternate design of a drug delivery apparatus in the form of a double balloon catheter positioned in a blood vessel.

FIG. 3 illustrates an alternate design for the catheter balloon utilizing a dual or concentric balloon concept. Specifically, a first, inner balloon 16 is provided which is constructed from a material such as polyethylene which is impermeable. The balloon 16 includes an inner chamber 17 which is connected through the inner balloon lumen 20 to the proximal end of the catheter. The embodiment of FIG. 3 is also provided with a second or outer balloon 18 which is generally concentric to the balloon 16 and which extends completely around the balloon 16. This outer balloon 18 is constructed from a permeable or semipermeable material similar to that of the balloon 12 of FIGS. 1 and 2 and includes a balloon chamber 19 formed between the outer surface of the balloon 16 and the inner surface of the balloon 18. The chamber 19 is connected through the outer balloon lumen 21 to the proximal end of the catheter. When using the structure of FIG. 3, the inflated balloon portion is first inserted into the arterial passageway until it bridges a stenotic lesion in the manner described above and known in the art. During the balloon inflation process contemplated by the structure of FIG. 3, the chamber 19 of the outer balloon 18 is first filled with the drug or fixative through the lumen 21. This is followed by inflation of the chamber 17 of the inner balloon 16 with standard inflation medium provided through the lumen 20. As a result of inflation of this inner balloon 16, sufficient pressure is developed against the chamber 19 to provide the pressure required to drive or transport the fixative through the outer balloon wall 18.

Although the structure of FIG. 3 shows a separate lumen 21 for filling the outer balloon chamber 19, it is contemplated that the lumen 21 could be eliminated and the chamber 19 prefilled with the fixative or other drugs. In such a structure, the pressure causing transport of the fixation solution across the balloon wall 18 would be provided solely by inflation of the inner balloon 16.

Figure 4:
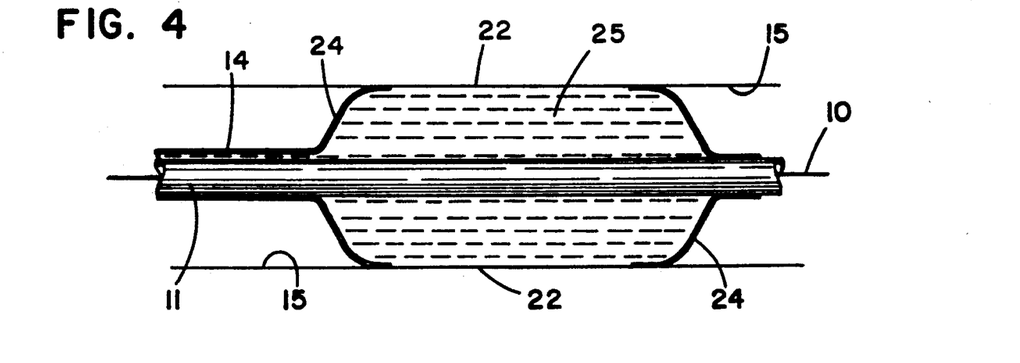
FIG. 4 is a fragmentary view, partially in section, of a further embodiment of the drug delivery apparatus of the present invention positioned in a blood vessel.
Figure 5:
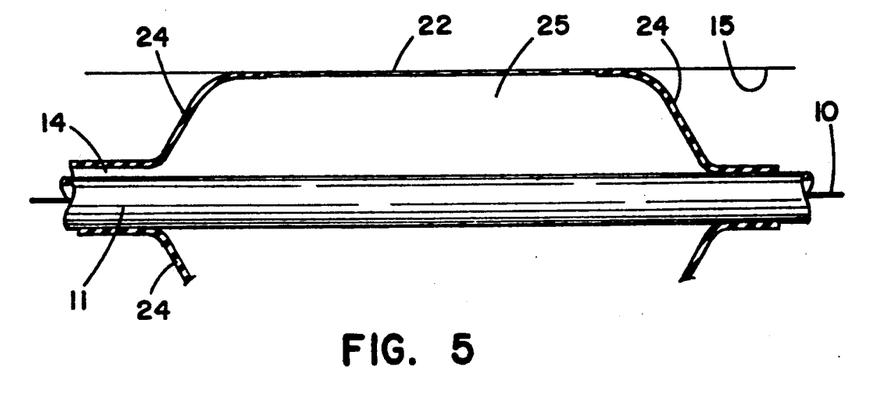
FIG. 5 is an enlarged fragmentary view, partially in section, of the embodiment of FIG. 4.

A further modified balloon structure is illustrated in FIGS. 4 and 5. The embodiment of FIGS. 4 and 5 is similar to the embodiment of FIGS. 1 and 2 except that the balloon structure in FIGS. 4 and 5 is constructed of two different materials. It will be appreciated that as an alternative, the balloon structure in FIGS. 4 and 5 can be constructed of a permeable material that is modified to have one or more impermeable portions (i.e., increased thickness). In FIGS. 4 and 5, the balloon end portions 24 are a totally impermeable material, while an intermediate portion 22 of the balloon positioned between the end portions 24 is a permeable or semipermeable material. The purpose of this structure is to enable more specific and precise delivery of the fixation solution or other drug desired to be administered. For example, with the end portions 24 constructed of an impermeable material, inadvertent passage of the fixation solution or other drug through such end portions is prevented. In the structure of FIGS. 4 and 5, the impermeable material may be polyethylene, or polyester or an area of permeable material that is functionally impermeable because of increased thickness or other modification that results in a non-permeable region or regions.

In the structure of FIGS. 4 and 5, the fixative or other drug is permitted to pass from the interior chamber 25 of the balloon only through the balloon portion 22. The material from which the portion 22 is constructed is similar to the material from which the balloon 12 of FIGS. 1 and 2 and the outer balloon 18 of FIG. 3 is constructed.

As a further alternative, the catheters of FIGS. 1–5 may be coated on their outer surfaces, or at least that portion of the outer surface which is to contact the vessel wall, with hydrogel to improve contact with the vessel wall. The hydrogel so described may also contain the fixative or drug to be delivered where solution passing from the catheter through the hydrogel will dissolve the fixative or drug and transport the fixative or drug to the vessel wall. As a further alternative, drug impregnated hydrogel may be coated on the inside wall of a catheter for similar drug delivery as solution passes through the hydrogel and catheter wall.

In the embodiments of FIGS. 1–5, pressure is the force which is utilized to transport the fixative or other drug from the interior balloon chamber across the balloon wall to the vessel wall. However, it is contemplated that other transport forces could also be used either with or in lieu of pressure to enhance or otherwise control the speed of drug transport. For example, one method could utilize DMSO as a carrier to transport a fixative or drug through the vessel wall. Other fluid diffusion enhancement compositions include propylene glycol, azone and ionic or non-ionic surfactants. Another method could utilize iontophoresis technology. Such technology is known in the art and is commonly used in transdermal drug delivery. In general, iontophoresis technology uses an electrical potential or current across a semipermeable barrier to drive ionic fixatives or drugs or drag nonionic fixatives or drugs in an ionic solution. Iontophoresis can be useful in certain applications of the present invention because it facilitates both transport of the fixative or drug across the selectively permeable membrane and enhances tissue penetration. In the application of iontophoresis, two electrodes, one on each side of the barrier, are utilized to develop the required potential or current flow. In particular, one electrode may be located inside of the catheter in opposed relation to the drug delivery wall of the catheter while the other electrode may be located at a remote site on a patient's skin. In addition to direct current, other wave forms may be utilized (e.g., a series of rectangular waves producing a frequency of 100 Hz or greater).

Figure 6:
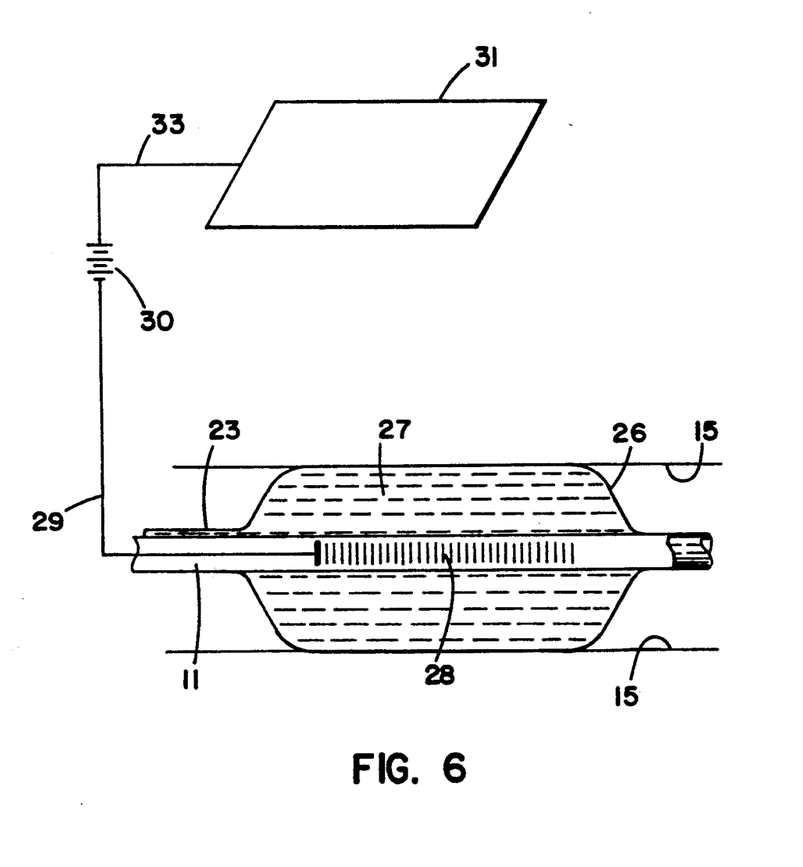
FIG. 6 is a fragmentary view, partially in section, of the drug delivery apparatus of the present invention positioned in a blood vessel and embodying iontophoresis means to transport the drug across the balloon surface.

The embodiment of FIG. 6 illustrates a structure utilizing iontophoresis to assist in driving the fixative or other drug across the balloon wall 26 and into contact with the vessel walls 15. In FIG. 6, one electrode 28, the catheter electrode, is located on or within the catheter body 11 while the other electrode 31, the body surface electrode, is located on the body surface or within the body of the patient. In order for iontophoresis techniques to be utilized, the fixative or other drug within the balloon chamber 27 requires specific characteristics. Ideally, such fixative or other drug should have an ionic nature or have other ionic molecules bound to the fixative or the active components of the drug to promote the iontophoretic movement or transport across the balloon wall 26. An electrical current for the iontophoretic process of FIG. 6 is produced between the electrodes 28 and 31 by an external power source 30 through the electrical leads 29 and 33, respectively.

During operation of the device of FIG. 6, the balloon 26 is first positioned across the stenotic lesion in the manner described above. The balloon interior 27 is then inflated with the fixative through the lumen 23. This is followed by activating the power supply 30, thereby creating a current between the electrode 28 and the electrode 31 which passes through the balloon wall 26. This current drives or drags the fixative or other drug within the chamber 27 across the wall and into contact with the surrounding vessel wall 15 and vascular tissue. The structure of FIG. 6 utilizes both pressure and iontophoresis as the driving force, although, it is contemplated that iontophoresis could be utilized alone.

It is contemplated that iontophoresis by itself, or in combination with a solvent like DMSO as a carrier, could yield fixative or drug transport into or through a vessel wall at pressures less than about 20 mm Hg above normal ambient vessel wall pressure and preferably at less than about 5 mm Hg, thereby avoiding substantial damage to the vessel wall known to occur at higher pressures.

The polarity of the iontophoretic electrodes may be reversed in order to recapture excess fixative or drug delivered to or through the vessel wall.

Figure 7:
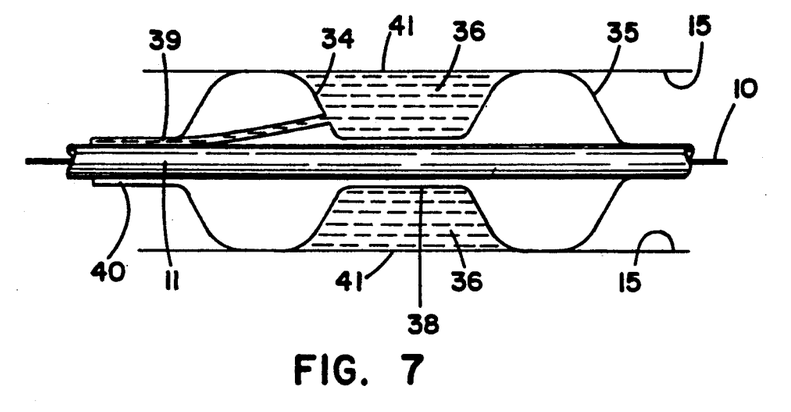
FIG. 7 is a fragmentary view, partially in section, of a still further alternate design of a drug delivery apparatus in accordance with the present invention positioned in a blood vessel and illustrating alternate means for defining the local area for drug delivery.

A further embodiment of a drug delivery apparatus in accordance with the present invention is illustrated in FIG. 7. FIG. 7 illustrates a further modified catheter balloon design which includes a double lobed balloon having a pair of spaced inflatable lobes 34 and 35. These lobes 34 and 35 are connected to a common interior chamber 38 which is in turn connected to a balloon lumen 40 extending to the proximal end of the catheter. The structure of FIG. 7 also includes a drug supply lumen 39 extending to the proximal end of the catheter and in communication with an area 36 formed between the balloon lobes 34 and 35.

During use of the structure of FIG. 7, the balloon is introduced into the vessel as described above in its deflated condition. After it has been positioned in that portion 41 of the vessel to which a drug is desired to be administered, the balloon lobes 34 and 35 are inflated by introducing an inflation medium through the lumen 40 and into the interior chamber 38. This inflation causes the lobes 34 and 35 to expand as illustrated so that their outer peripheral portions engage the inner surfaces of the vessel walls 15. Such engagement defines a drug treatment zone between the lobes 34 and 35. A desired drug is then introduced into the chamber 36 through the lumen 39 so that such drug is in direct contact with the vessel wall 15.

Figure 8:
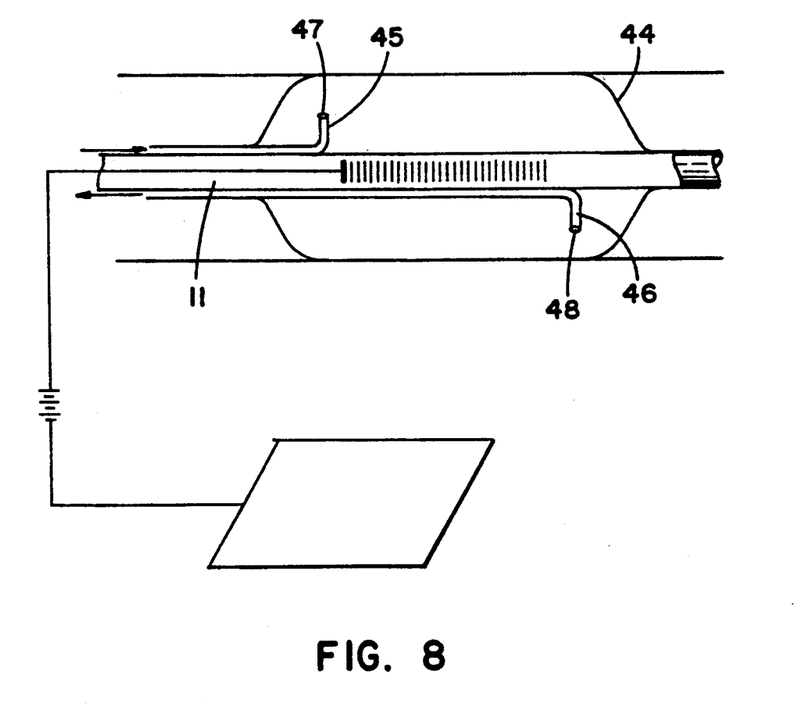
FIG. 8 is a fragmentary view, partially in section, of the drug delivery apparatus of the present invention positioned in a blood vessel, embodying iontophoresis to transport a drug across the balloon surface where the solution containing the drug is circulated through the balloon.

A still further embodiment of a drug delivery apparatus in accordance with the present invention is illustrated in FIG. 8. This embodiment would be useful for delivery of a fixative, but would be particularly useful for delivery of antitumor drugs. FIG. 8 illustrates a modified catheter balloon design having a balloon 44 positioned on catheter body 11 near its distal end. One delivery lumen or passageway 45 extends along the catheter body 11 to the proximal end of the body 11 and a recovery lumen or passageway 46 also extends along the catheter body 11 to the proximal end, said delivery lumen 45 and recovery lumen 46 useful for circulating solution containing a fixative or drug to and from the catheter balloon. The outlets 47 and 48 may be positioned in the balloon to achieve optimal circulation within the balloon. This embodiment may be most useful in delivering antitumor drugs which are difficult to dissolve where the delivery solution accordingly is very low in concentration of the antitumor drug and easily depleted of such drug. Circulation in this case would be important for continuous delivery over long time periods. This embodiment may be combined with reversing the polarity of the electrodes of iontophoresis in order to remove excess drug after treatment.

In addition to the embodiment of FIG. 8, the embodiments of FIGS. 1-7, illustrated principally for delivery of a fixative to a vessel wall, can also be useful in delivering any drug to or through a vessel wall. In particular, each of the above embodiments of FIGS. 1-8 may be used for such drug delivery and each embodiment would be useful for delivering an antitumor, antihyperplastic or other agent through a vessel wall to a nearby or adjacent tumor or other internal body tissue. For example, a drug may be delivered substantially transversely to the longitudinal axis of a body passageway in order to treat a localized region of tissue located adjacent to the passageway. This is illustrated by using iontophoresis to drive, or DMSO to carry, through the passageway wall and into the surrounding or adjacent tissue. Any of the foregoing alternative embodiments of the apparatus as seen in FIGS. 1-8 may also be used for such drug delivery.

In particular, tumors may be treated by delivering certain drugs through blood vessels or the intestinal tract or whatever to adjacent tumor sites. Without limiting the invention, the following table discloses certain drugs well suited for such delivery to the described tumors. Further, the present invention is well suited to delivery of sensitizer and immunomodulator drugs.

TABLE 1

| Drug | Major Indications |
| --- | --- |
| Mechlorethamine | Hodgkin's and non-Hodgkin's lymphomas, topical solution in mycosis fungoides, sclerosing agent for malignant pleural effusions |
| Cyclophosphamide | Hodgkin's and non-Hodgkin's lymphoma, multiple myeloma, neuroblastoma, Ewing's sarcoma, small cell carcinoma of lung, breast cancer, ovarian cancer, testicular cancer |
| Chlorambucil (Leukeran) | Chronic lymphocytic leukemia, Hodgkin's and non-Hodgkin's lymphomas, carcinomas of the breast and ovary, choriocarcinoma |
| Melphalan (Alkeran) | Multiple myeloma, polycythemia vera, carcinomas of the ovary and breast |
| Busulfan (Myleran) | Chronic myelogenous leukemia, polycythemia vera |
| Dacarbazine (DTIC) | Hodgkin's and non-Hodgkin's lymphomas, sarcomas, melanoma |
| Cisplatin (Platinol) | Testicular, ovarian, head and neck, and gastric carcinomas |
| Methotrexate | Acute lymphoblastic leukemia, carcinomas of the head and neck, ovary, breast, testis, small cell carcinoma of the lung, choriocarcinoma, osteosarcoma, mycosis fungoides |
| 6-Mercaptopurine 6-MP | Acute leukemias |
| Thioguanin 6-TG | Acute leukemias |
| 5-Fluorouacil (5-FU) | Carcinomas of the gastrointestinal tract, breast, and ovary |
| Vinblastine (Velban) | Hodgkin's and non-Hodgkin's lymphomas, acute lymphoblastic leukemia, carcinomas of the breast and testes, Wilms' tumor, neuroblastoma |
| Dactinomycin | Wilms' tumor, neuroblastoma, embryonal rhabdomyosarcoma, Ewing's sarcoma, choriocarcinoma, carcinoma of the testes, carcinoid tumors |
| Doxorubicin | Acute leukemias; sarcomas; Hodgkin's and non-Hodgkin's lymphomas; carcinomas of the breast, ovary, head, neck and thyroid; Ewing's sarcoma; small cell carcinoma of the lung |
| Daunorubicin | Acute leukemias |
| Mitomycin (Mutamycin) | Carcinomas of gastrointestinal tract, breast, head, and neck |
| Diethylstilbestrol | Carcinomas of the prostate and breast |
| Retinoic acid and analogues | Dermal hyperplasia |

For the purposes of primary or adjuvant treatment or other circumstances where drug delivery to a specific local or regional internal body tissue site such as a solid tumor, abscess, regional lymph nodes or the like is desired, further embodiments of the present invention as shown in FIGS. 9 and 10 are preferred. The tissue delivery system shown in FIGS. 9 and 10 includes a drug delivery apparatus 60 that is positioned into a specific tissue, such as a tumor.

As seen in FIG. 9, a preferred drug delivery apparatus 60 for treating an internal body tissue includes a flexible catheter body 11' and drug delivery component 69 having a drug delivery passageway 64 including an outer wall 66, and an outer selectively permeable membrane portion 67 proximate the distal end 61. The outer selectively permeable membrane 67 prevents escape of the drug from passageway 64 and drug delivery component 69 until the desired time of delivery. It is to be understood that the selectively permeable membrane 67 also controls the rate of release of the drug. The drug is then driven across membrane 67 by a pressure gradient and/or voltage gradient (iontophoresis), or other force. In a preferred embodiment for iontophoresis, selectively permeable membrane 67 material is a dialysis membrane, nylon, or polysulfone. Drug delivery passageway 64 of drug delivery component 69 extends from proximal end 63 to distal end 61 of apparatus 60. As seen in FIGS. 9 and 10, preferably, drug delivery component 69 is coaxially aligned about catheter body 11'. It is to be appreciated that drug delivery component 69 can be connected with catheter body 11' by a variety of adjacent configurations by one of skill in the art.

The embodiment seen in FIG. 9 illustrates selectively permeable membrane 67 affixed to a portion of outer wall 66 having at least one opening 68 that facilitate fluid transfer through outer wall 66 of passageway 64 to membrane 67. Alternatively, as seen in FIG. 10, selectively permeable membrane 67 can form an integral portion of outer wall 66. As seen in both FIGS. 9 and 10, to position apparatus 60 over the shaft of an introducer such as a probe, needle or trocar (not shown) introducer lumen 65 through the center of catheter body 11' is provided. It is to be understood that apparatus 60 can range in size from very large (trocar) to very small (tenths of mm), depending on the type and location of internal body tissue to be treated.

The embodiments of apparatus 60 in FIGS. 9 and 10 utilize iontophoresis to assist in driving the drug across selectively permeable membrane 67. To deliver a drug to a target area of an internal body tissue, iontophoresis is preferred because it facilitates both transport of a fixative or drug across the selectively permeable membrane and enhances tissue penetration. If iontophoresis is used, then similarly to the structure seen in FIG. 6, one electrode 28', the catheter electrode, is located on or within catheter body 11', while the other electrode (31) is located on the body surface of the patient. The other electrode may in certain applications be positioned at other regions of the patient including appropriate internal areas.

As an alternative to the embodiments seen in FIGS. 9 and 10 using iontophoresis to deliver a drug to a target area, the tissue delivery system of the present invention can use pressure as the force to transport a drug to a target area of internal body tissue. For this purpose, regulation means known to those skilled in the art (e.g., compressor, regulator or syringe pump) can be used to apply sufficient pressure to deliver the drug to the target area. Those of skill in the art will recognize that the pressure applied will be adequate to drive the drug across selectively permeable membrane 67 to the target area without further traumatization of the internal body tissue to be treated.

As described earlier with respect to the embodiments shown in FIGS. 1–5, other transport forces can be used either with or in lieu of pressure to enhance or otherwise control the speed of drug transport to an internal body tissue according to the present invention. For example, one of skill in the art could utilize DMSO, propylene glycol, azone, or various surfactants as a carrier to transport the drug through selectively permeable membrane portion 67 to the target area of internal body tissue.

For treatment of an internal body tissue according to the present invention, the introducer (not shown) is placed into the target area, which may be a tumor or the like, after identification of the position of the lesion mechanically, radiographically, thermally, ultrasonically, or through some other like methodology. The trocar./probe can be designed for steerability to facilitate positioning into the tumor. This can be accomplished by simply placing a bend in the trocar or by other mechanical design techniques known to those skilled in the art.

The active apparatus 60 is then passed through or over the introducing element directly over the inducer or through the void left in the intervening tissue by the withdrawal of the introducer. After apparatus 60 is in place, as confirmed by one of the foregoing methods, the active compound is delivered through passageway 64 into drug compartment 69 and across membrane 67 into the local or regional tissue. Using an embodiment of apparatus 60 of the type seen in of FIGS. 9 or 10, the delivery is accomplished iontophoretically. The active compounds delivered to an internal body tissue using apparatus 60 include, but are not limited to, antitumor agents such as the vinca alkaloids, anthracycline antibiotics, platinum analogs, antimetabolites (e.g., methotrexate); antibiotics; sensitizers or other compounds such as those exemplified in Table 1, herein.

The advantage of this method is that it allows delivery of the drug into the interstitial fluid and into the cells of the target area themselves even if the vasculature of the area is severely compromised and the cells do not preferentially take up the drug. These phenomena are a well-known attribute of solid tumors and constitute one of the most significant barriers to the treatment of such cancers.

In addition to delivery of antitumor agents to internal tissues, the usefulness of the present apparatus and method for the treatment of other diseases of internal tissue will be appreciated by those skilled in the art.

In the case of both the vascular delivery embodiment (FIGS. 1–8) and tissue delivery embodiment (FIGS. 9 and 10) described herein phonophoresis (sometimes referred to as sonophoresis) can be used as an alternative transport force. Similarly, in the case of the embodiments shown in FIGS. 11–14, an active transport force--either iontophoresis or phonophoresis--can be employed. Phonophoresis is the use of ultrasonic or high frequency sound waves to transport drugs. As used in the present invention, phonophoresis can be used to transport drugs through the selectively permeable membrane and into the surrounding tissue. For certain therapeutic procedures, phonophoresis has several advantages over iontophoresis, including the ability to achieve greater penetration and to more readily deliver an entire molecule, rather than an ionically charged form of the drug. All prior applications of phonophoresis have been limited to transdermal delivery of drugs. It has primarily been used to deliver anti-inflammatory agents and local anesthetics through the skin in treating epicondylitis, tendonitis, bursitis and osteoarthritis. It is also well-suited for driving fixatives or drugs across the catheter of this invention to localized body passageways or internal tissues because it facilitates both transport of a fixative or drug across the selectively permeable membrane and enhances tissue penetration. In addition to drug delivery, ultrasound may be advantageously used with the catheter of the present invention based on the increased tissue temperature, tissue hyperemia and increased capillary permeability associated with ultrasound. These actions can enhance intra-tissue drug transport and cellular uptake as well as cause vasodilation/relaxation which may be beneficial in vascular drug applications using catheter embodiments of the type described herein.

When phonophoresis is used with either the vascular delivery embodiment or tissue delivery embodiment of the catheter of the present invention, the cathode electrode 28 of FIG. 6 is replaced by an ultrasonic piezoelectric transducer (barium titanate, lead zirconate titanate, or the like), which is connected to the external power source 30 and placed within the catheter opposite the drug delivery wall. The ultrasonic transducer is activated to enhance transport of drugs or fixatives into tissue surrounding the catheter. The diffusion rate of drugs delivered by phonophoresis depends upon the intensity and frequency of the ultrasonic field. Prior transdermal applications of phonophoresis use intensities of 0.1 to 6 watts/cm and involve direct correlation between the amount of drug diffused and the intensity of the ultrasonic field. Internal applications (not requiring transdermal delivery) of phonophoresis with the catheter embodiments of the present invention are envisioned to require significantly less intensity to deliver an equal amount of drug. Various frequencies can be used. A frequency of about 1 MHz has been optimally used in transdermal phonophoresis. It is envisioned that approximately 1 MHz or less can be used for internal applications of the catheter embodiments described herein.

Figure 11:
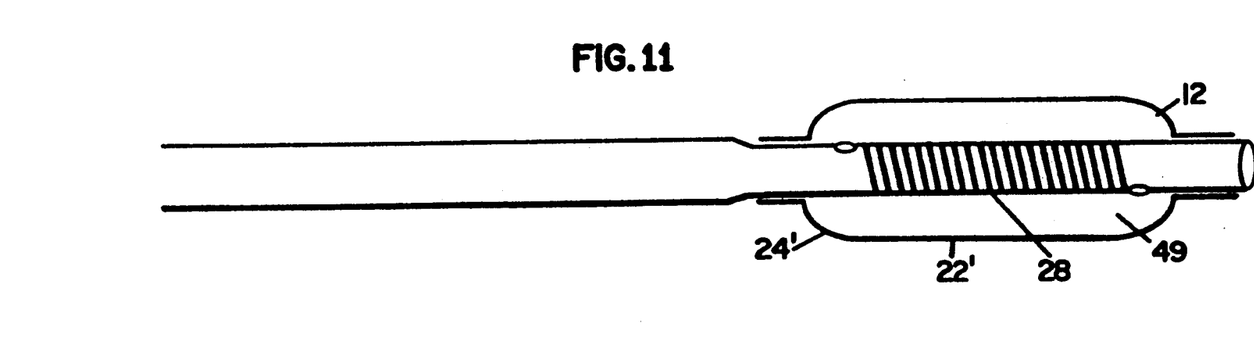
FIG. 11 is a fragmentary view, partially in section, of a still further alternate design of a drug delivery apparatus in accordance with the present invention in the form of a catheter with a drug delivery component to transport a drug to internal body tissue.
Figure 13:
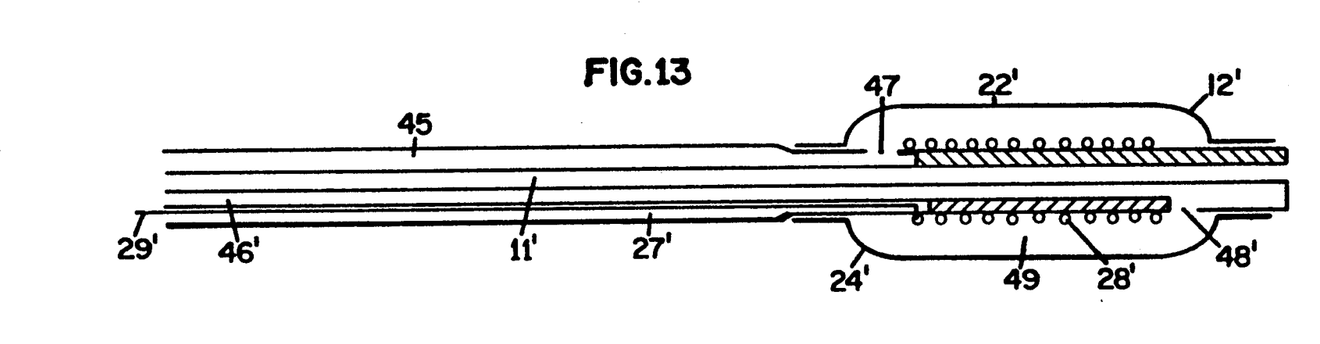
FIG. 13 is a fragmentary view of a modified iontophoretic embodiment of the drug delivery apparatus shown in FIG. 11.
Figure 14:
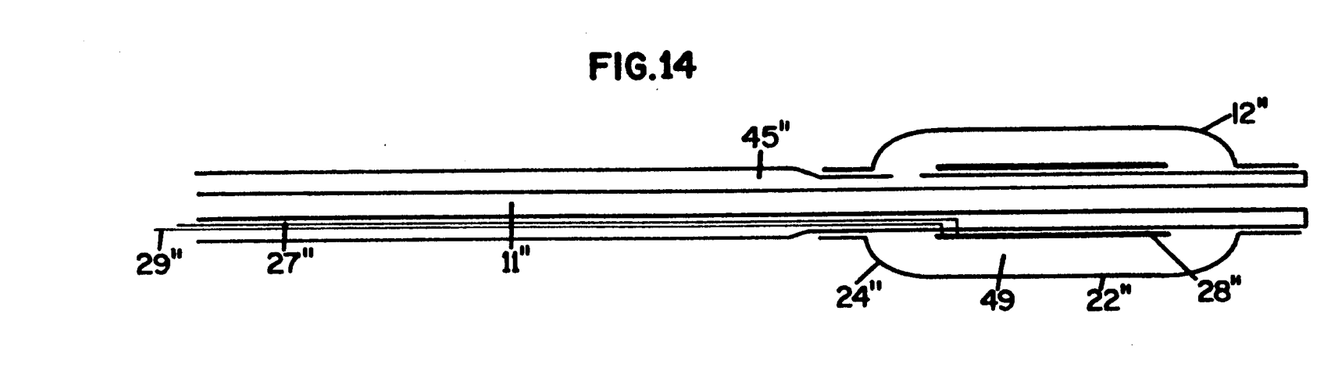
FIG. 14 is a fragmentary view of a further modified phonophoretic embodiment of the drug delivery apparatus shown in FIG. 11.

According to the present invention, further catheter embodiments are envisioned employing a selectively permeable microporous membrane portion of the drug delivery component, together with an active, non-pressure, transport force for assisting the delivery of the drug to a body tissue (FIGS. 11, 13, and 14). In these embodiments, the microporous membrane, in conjunction with the active delivery mechanisms, aids in controlling drug transfer from the catheter by minimizing passive diffusion or flow under the slight pressure involved in filling the drug chamber or inflating the balloon to make contact with a vessel wall. However, drug delivery into the tissue under active iontophoretic or phonophoretic delivery will not be inhibited by the membrane.

The microporous material provides more uniform delivery areas, which will provide more uniform drug distribution into the surrounding tissue, will reduce the potential for areas of high current densities during iontophoresis (associated with a few larger pores), and will decrease the potential for tissue damage or breakdown of the membrane material due to high current density.

The numerous micropores will reduce the likelihood that a significant portion of the membrane could become blocked with blood components, secretions, lubricants, or other material. In addition, blood or other secretions will not cross the microporous membrane and enter the drug chamber during deflation of the balloon. The microporous material will also allow rapid balloon deflation without blood reflux into the catheter, which is an important feature in coronary arterial applications. Finally, the microporous material will allow the use of a neutral or charged membrane surface to promote or control drug transfer and delivery.

Figure 12A:
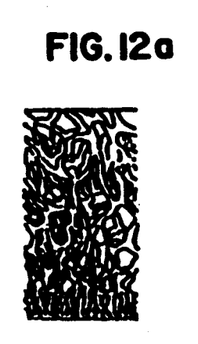
Figure 12B:
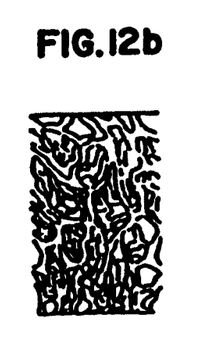

As seen in FIGS. 11, 13, and 14, the selectively permeable membrane has a selectively permeable microporous membrane portion 22'. A schematic structure for the microporous membrane is illustrated in FIGS. 12a and 12b. Particularly, the selectively permeable microporous membrane can have either an isotropic (asymmetric) or symmetric structure. The pore size of the membrane can vary from about 10 Å to 10,000 Å (i.e., 1 micron).

The microporous membrane that satisfies the requirements of the invention can be manufactured in any of several ways, most of which are readily understood by those skilled in the art of manufacturing microfiltration and ultrafiltration membranes. These techniques include, for example:

---
1. A phase inversion process in which an appropriate polymer solution is coagulated in a nonsolvent quench bath can be employed.
2. A thermal inversion process can be used whereby a polymer solution or mixture at elevated temperatures can be coagulated by a reduction in temperature, under controlled conditions, to form a microporous membrane.
3. A so-called track-etch process whereby a polymer film is bombarded by protons, electrons, radiation, etc. and then subsequently subjected to a controlled etching can be used as well.
4. A laser may be used to form holes or pores of the desired size in a polymeric material.
---

In both processes 1 and 2, conditions can result in either a symmetric or an asymmetric membrane being formed. Either type of membrane can be useful, although a preference may exist for one or the other in a given application. Any post-treatment of the membranes, such as irradiation, chemical grafting, coatings, etc. that would render the membrane more hydrophilic, fouling resistant, form a thin-film composite membrane or impart any other desirable properties would be a possible supplement to the above-mentioned formation processes. These processes are examples of methods that can be used to form a membrane of the desired properties. However, any additional methods that currently exist or that may become apparent that produce the desired membrane properties should also be included in the possible membrane formation mechanisms.

There are several forms or geometries into which these membranes can be made. A flat sheet membrane can be cast and then formed into a balloon shape or cylinder by gluing, sonic welding, etc. Additionally, a hollow fiber membrane can be spun or a tubular membrane cast that can be used as is or processed into a balloon by blow molding or some other balloon-forming process. A third option is to cast the membrane directly into a balloon shape by spin-casting or some other process that allows the desired shape to be achieved. During this processing, a membrane support can be used if desired or required.

One embodiment of the present invention incorporating a selectively permeable microporous membrane is shown in FIG. 13. This embodiment includes a drug delivery component in the form of a balloon 12' which contacts the body tissue for drug delivery. The balloon 12' is preferably made of an inelastic material such as polyester, polyolefin, a fluorpolymer, or the like. Preferably, the balloon 12' includes a selectively permeable microporous membrane portion 22, and a non-permeable section 24' as best shown in FIGS. 11 and 12. As shown in FIGS. 13 and 14, the drug delivery component is formed proximate the distal end of the catheter and includes an active, non-pressure transport force such as iontophoresis (FIG. 13) or phonophoresis (FIG. 14).

One embodiment of a drug delivery apparatus having a selectively permeable microporous membrane, together with an iontophoretic driving force, is shown in FIG. 13. In FIG. 13, the drug delivery apparatus includes an electrode 28 within the balloon 12'. Drug is delivered to the balloon 12' through a drug input lumen 45' and an input port 47'. The embodiment shown in FIG. 13 further includes a drug recovery lumen 46, in fluid communication with the drug delivery component 49 through drug recovery port 48'. The embodiment in FIG. 13 further shows a conductor lumen 27 for the electrode wire/conductor 29'. The conductor 29' could alternately be inserted along one of the drug lumens or extruded into the catheter wall.

It will be understood that the embodiment in FIG. 13 can be constructed without a drug recovery lumen, if desired. Also, FIG. 13 shows a guide wire lumen 11 which may be omitted, depending on the intended medical use of the device, such as urological applications.

The embodiment in FIG. 14 illustrates a further embodiment of a drug delivery apparatus including a selectively permeable microporous membrane which includes a phonophoretic driving force including a transducer 28', which is connected by conductors 29', shown in the conductor lumen 27". As in the case of FIG. 13, the drug delivery apparatus in FIG. 14 includes a drug delivery lumen 45" and lumens for the guide wire and conductor 11", 27". It will be understood that the guide wire and conductor can be optionally excluded depending on the intended use of the drug delivery apparatus.

Although the description of the preferred embodiment and method have been quite specific, it is contemplated that various modifications could be made without deviating from the spirit of the present invention. For example, a fixative or other drugs may be delivered to the walls of an artery, perhaps already dilated, through a catheter balloon wall which is perforated. An antitumor drug may be similarly delivered through a perforated balloon wall for delivery through a vessel wall to an adjacent tumor. Such perforated balloon may be combined with iontophoresis or phonophoresis to drive the drug into or through the vessel wall. Further, a drug can be delivered to an internal body tissue through a selectively permeable membrane portion of a drug delivery component connected to a catheter. When the catheter and connected drug delivery component are directed to a body tissue target area over a rigid probe or trocar the amount of drug delivered to the tissue to be treated is maximized and the leakage of drug back along the catheter and away from the target area is minimized. Accordingly, it is intended that the scope of the present invention be dictated by the appended claims, rather than by the description of the preferred embodiment and method.

We claim:

1. A drug delivery apparatus having a distal end and a proximal end for local delivery of a drug to internal body tissue comprising:
   (a) a flexible catheter for insertion into an internal target area of a body;
   (b) drug delivery means connected to said catheter for delivering a drug to said target area, said drug delivery means having a fluid delivery passageway for delivering said drug to said distal end, an outer wall and a selectively permeable microporous outer membrane portion proximate said distal end of said drug delivery apparatus, said microporous outer membrane further comprising pores sized from about 10 Å to about 1 micron and at least one impermeable end portion to enhance precise delivery of said drug to said internal target area; and
   (c) phoresis means for assisting the transport of said drug across said selectively permeable microporous outer membrane.

2. A drug delivery apparatus according to claim 1 wherein said outer of said drug delivery means further comprises one or more openings to provide fluid communication from said fluid delivery passageway to said outer membrane portion.

3. The drug delivery apparatus of claim 1 wherein said selectively permeable outer membrane portion forms part of said outer wall.

4. A drug delivery apparatus according to claim 1 wherein said drug delivery means is coaxially aligned about said flexible catheter.

5. A drug delivery apparatus according to claim 1 wherein said catheter body includes an integral introducer.

6. A drug delivery apparatus according to claim 1 wherein said microporous outer membrane pore sizes range from about 600 Å to about 1 micron.

7. A drug delivery apparatus according to claim 1 wherein said drug delivery means further includes a drug recovery lumen extending from said drug chamber to the proximal end of said flexible catheter.

8. A drug delivery apparatus according to claim 1 wherein said means for assisting transport of said drug is a phonophoresis means.

9. The drug delivery apparatus of claim 8 wherein said phonophoresis means is an ultrasonic transducer.

10. A drug delivery apparatus according to claim 1 wherein said means for assisting transport of said drug is an iontophoresis means.

11. The drug delivery apparatus of claim 10 wherein said iontophoresis means is an electrode.

12. A drug delivery apparatus for local delivery of a drug to an internal body passageway having an elongated passageway wall comprising:
   (a) a flexible catheter having a distal end and a proximal end;
   (b) drug delivery means connected to said catheter for delivery of a drug to said passageway wall, said drug delivery means comprising a balloon near said distal end of said flexible catheter for engagement with a local area of said passageway wall, said balloon having an outer wall with a selectively permeable microporous membrane portion and a drug delivery chamber within said balloon, a drug delivery lumen extending from said drug delivery chamber to said proximal end of said flexible catheter and a drug recovery lumen extending from said drug delivery chamber to said proximal end of said flexible catheter, said microporous membrane portion of said outer wall further comprising pores sized from about 10 Å to about 1 micron and at least one impermeable end portion to enhance precise delivery of said drug to said local area of said passageway wall; and
   (c) phoresis means for assisting the transport of said drug across said selectively permeable microporous membrane portion of said outer wall.

13. A drug delivery apparatus according to claim 12 wherein said microporous membrane pore sizes range from about 600 Å to about 1 micron.

14. A drug delivery apparatus according to claim 12 wherein said means for assisting transport of said drug is a phonophoresis means.

15. The drug delivery apparatus of claim 14 wherein said phonophoresis means is an ultrasonic transducer.

16. A drug delivery apparatus according to claim 12 wherein said means for assisting transport of said drug is an iontophoresis means.

17. The drug delivery apparatus of claim 16 wherein said iontophoresis means is an electrode.

* * * * *

UNITED STATES PATENT AND TRADEMARK OFFICE
CERTIFICATE OF CORRECTION

PATENT NO. : 5,286,254

DATED : February 15, 1994

INVENTOR(S) : James E. Shapland et al.

It is certified that error appears in the above-identified patent and that said Letters Patent is hereby corrected as shown below:

On the title page, item [75] Inventors:, add the name of Joel R. Racchini, Edina, Minn.

At column 13, line 33, delete "." after --trocar--

At column 16, line 23, for "22" read --22'--.

At column 16, line 37, for "46" read --46'--.

At column 16, line 53, for "28'" read --28"--.

At column 16, line 53, for "29'" read --29"--.

Signed and Sealed this

Fifth Day of March, 1996

Attest:

BRUCE LEHMAN

*Attesting Officer*  *Commissioner of Patents and Trademarks*